(12) United States Patent
Carberry et al.

(10) Patent No.: US 10,227,557 B2
(45) Date of Patent: Mar. 12, 2019

(54) METHOD AND APPARATUS FOR PRODUCING ASTAXANTHIN (71) Applicant: Sustainable Aquatics, Inc., Jefferson City, TN (US)

(72) Inventors: John Carberry, Talbott, TN (US); Matthew John Carberry, Talbott, TN (US); Dennis Steven Tagrin, Jefferson City, TN (US)

(73) Assignee: Sustainable Nutrition, Inc., Knoxville, TN (US)

( * ) Notice: Subject to any disclaimer, the term of this patent is extended or adjusted under 35 U.S.C. 154(b) by 151 days.

(21) Appl. No.: 14/847,829

(22) Filed: Sep. 8, 2015

(65) Prior Publication Data

US 2016/0075989 A1  Mar. 17, 2016

Related U.S. Application Data (60) Provisional application No. 62/050,318, filed on Sep. 15, 2014.

(51) Int. Cl.
  *C12N 1/12*    (2006.01)
  *C12P 23/00*   (2006.01)
  *C12N 13/00*   (2006.01)

(52) U.S. Cl.
  CPC ............... *C12N 1/12* (2013.01); *C12N 13/00* (2013.01); *C12P 23/00* (2013.01)

(58) Field of Classification Search
  None
  See application file for complete search history.

(56) References Cited

U.S. PATENT DOCUMENTS 6,022,701 A  2/2000 Boussiba et al.
6,406,735 B2 6/2002 Stein et al.
(Continued)

FOREIGN PATENT DOCUMENTS

EP    1681060       *  7/2006
WO    2006/034556      4/2006

OTHER PUBLICATIONS

Miao et al., Chin. J. Oceanol. Limnol. 31(6): 1181-1189 (2013). (Year: 2013).*

(Continued)

*Primary Examiner* — Erin M. Bowers
(74) *Attorney, Agent, or Firm* — Pitts & Lake, P.C.

(57) ABSTRACT

A method for producing astaxanthin incorporates a method for producing astaxanthin-rich algae cells and a method for extracting astaxanthin therefrom. An initial feedstock comprises healthy algae, water, and nutrients. During a growth phase, carbon dioxide and light from a light source are supplied to the feedstock, thereby amplifying the algae. At least a portion of the nutrients remaining after amplification of the algae are separated from the amplified algae. During a stress phase, carbon dioxide and light are supplied to the amplified algae, thereby promoting production of astaxanthin by the amplified algae. The amplified algae and a cover are placed within an interior of an attrition mill having interior surfaces and media which are substantially non-reactive to astaxanthin and milled to release the astaxanthin from the algae. The cover limits oxidation of the released astaxanthin.

16 Claims, 6 Drawing Sheets

(56) References Cited

U.S. PATENT DOCUMENTS

2004/0091524 A1* 5/2004 Tanaka .................. C07C 403/24
424/464
2007/0269526 A1* 11/2007 Bos ...................... A23D 7/0053
424/502

OTHER PUBLICATIONS

Shin et al., Ceramics Int'l 39: 8963-8968 (2013). (Year: 2013).*
Katsuda, T et al, Effect of Flashing Light from Blue Light Emitting Diodes on Cell Growth and Astaxanthin Production of Haematococcus pluvialis, Journal of Bioscience and Bioengineering, 2006, pp. 442-446, vol. 102, No. 5, DOI 10.1263/jbb, 102.442.
Kim, ZH et al., Enhanced Production of Astaxanthin by Flashing Light Using Haematococcus pluvialis, Enzyme and Microbial Technology, 2006, pp. 414-419, vol. 39, DOI: 10.1016/j.enzmictec.2005.11.041.
Petrusevski, B et al., Tangential Flow Filtration: A Method to Concentrate Freshwater Algae, Water Research, May 1995, pp. 1419-1424, vol. 29, No. 5, DOI: 10.1016/00431354(94) 00269D.
Kang, CD et al., Direct Extraction of Astaxanthin from Haematococcus Culture Using Vegetable Oils. Biotechnol Lett., Mar. 2008, pp. 441-444, vol. 30, No. 3.
Patent Cooperation Treaty, Int'l Search Report & Written Opinion, Form PCT/ISA/220 (Jul. 2014), dated Feb. 16, 2016.
Majewski et al., Extraction of Astaxanthin from Haematococcus Pluvialis by Supercritical Carbon dioxide. Univ. de La Serena, Fac. de Ingenier.
Machmudah et al., Extraction of Astaxanthin from Haematococcus pluvialis Using Supercritical CO2 and Ethanol as Entrainer. Ind. Eng. Chem. Res. 2006, 45, 3652-3657.
Rivera et al., Influence of Sample Processing on the Analysis of Carotenoids in Maize. Molecules 2012, 17, 11255-11268.
Aquasearch Inc. Analysis of Total Astaxanthin in algae meal prepared from Haematococcus pluvialis. Aquasearch Inc., 1999.
Dong et al., Four Different Methods Comparison for Extraction of Astaxanthin from Green Alga *Haematococcus pluvialis*. Scientific World Journal vol. 2014.
Ni et al., Optimization of acidic extraction of astaxanthin from Phaffiarhodozyma. Journal of Zhejiang University Science B, 2008.
Dong et al, In situ carbon dioxide fixation in the process of natural astazanthin production by mixed culture of Haematococcus pluvialis & phaffia rhodozyma, Catalysis Today, vol. 98, No. 4, Dec. 14, 2004 pp. 537-544.
Oncel S.S. et al, Comparison of different cultivation modes & light intensities using mono-cultures & co-cultures of Haematococcus pluvialis & chlorella zofingiensis, Journal of Chemical Technology & Biotechnology, vol. 86, Mar. 8, 2011 p. 414-420.
Rosa A. et al, Omega-3 fatty acid composition and biological activity of three microalgae species, International Journal of Food, Agriculture & Environment, vol. 3, Apr. 1, 2005, p. 120-124.
Barros M.P. et al, Combined astaxanthin & fish oil supplementation improves glutathione-based redox balance in rat plasma & neutrophils, Chemico-Biological Interactions, vol. 197, Mar. 10, 2012, p. 58-67.
Chekanov K. et al, Accumulation of Astaxanthin by a new haematococcus pluvialis strain BM1 from the white sea coastal rocks (Russia), Marine Drugs, vol. 12, Aug. 15, 2014 p. 4504-4520.
Norsker N. H. et al, 17. Microalgal Biotechnology in the Production of Nutraceuticals, Biotechnology in Functional Foods and Nutraceuticals, 2010, CRC Press—Taylor & Francis Group, p. 279-312.
European Patent Office, Supplemental European Search Report, Form EPO 1503, dated Jan. 30, 2018.

\* cited by examiner

METHOD AND APPARATUS FOR PRODUCING ASTAXANTHIN

CROSS-REFERENCE TO RELATED APPLICATIONS

This application claims the benefit of U.S. Provisional Patent Application Ser. No. 62/050,318, filed on Sep. 15, 2014, which is incorporated herein in its entirety by reference.

STATEMENT REGARDING FEDERALLY-SPONSORED RESEARCH OR DEVELOPMENT

Not Applicable

BACKGROUND OF THE INVENTION

1. Field of Invention

The present general inventive concept relates to an improved process for producing astaxanthin and astaxanthin-rich algaes and extracts useful as a pharmaceutical, nutraceutical, human or animal food ingredient and for larval fish nutrition.

2. Description of the Related Art

Astaxanthin, a keto-caratonoid, is a phytochemical known as a terpene. Astaxanthin is highly desired as a feed additive in agriculture and aquaculture, as it provides the color and certain antioxidant mechanisms for several fish and animal meats. For example, astaxanthin contributes to the color and antioxidant properties of egg yolks. In nature, animals such as shrimp, krill, zooplankton, and salmon take up and display astaxanthin in their color, and astaxanthin contributes to the antioxidant value of their flesh or biomass. Astaxanthin also provides the red color of various other fish meats, such as trout and several cooked shellfish, such as shrimp, lobster, and the like. Astaxanthin has also become very popular as a pharmaceutical and nutraceutical ingredient.

Astaxanthin occurs naturally, for instance in bacteria, yeasts, and algaes. Haematococcus pluvialis, a fresh water algae, is the largest and most productive known source for producing natural astaxanthin. Astaxanthin concentrations in Haematococcus pluvialis are known to exceed 40,000 parts per million. However, the supply of natural astaxanthin from Haematococcus pluvialis, which consists of only a single stereoisomer, is less than market demand. Astaxanthin is available from several sources and by manufacture of a synthetic production process. However, this results in a mixture of stereoisomers and does not produce the same color in feeds as is desired.

Current production processes for making astaxanthin via controlled growth of algae typically involve setting up a growth phase of algae, typically Haematococcus pluvialis, often in ponds or bioreactors filled with water. Such bioreactors can be indoors using artificial light sources or outdoors using natural sunlight. During this stage of production, typically 8 to 10 days or longer, nutrition is added to the water, such as nitrates, phosphates, sodium and silicates, and the algae is allowed to grow. The grown algae is then subjected to a shock phase in which the algae is subjected to stress, thereby promoting the production of astaxanthin by the algae. Typically, such stress is accomplished by subjecting the algae to nutritional withdrawal in conditions otherwise optimal for photosynthesis, i.e., in the presence of sufficient moisture, warmth, light, and carbon dioxide, and absent competition from other species. For example, in one prior art process, the algae and water is put into a pond with recirculating raceways in an outdoor environment. In these raceways, the gas/water intermix is less than desirable for growth of the algae and turbulence is much less than desirable. Following the shock phase, the algae containing an amount of astaxanthin is harvested. This harvesting process is typically done in three stages. First, the algae and water mixture is centrifuged to remove water. Then, the algae is milled and/or treated with acid to break the algae cells and liberate the astaxanthin. Finally, the broken algae and astaxanthin mixture is spray dried or otherwise prepared for packaging.

The above-described processes for making astaxanthin have several inherent limitations. For example, high losses, cell destruction and death during the growth phase and the stress phase of Haematococcus pluvialis results in low yields of astaxanthin as a percentage of total algal biomass. Whereas astaxanthin should approach or exceed 4% of biomass during the stress phase, it is often much lower due to death and destruction of algae cells. The stress phase, in which the algae cells under stress produce astaxanthin, is understood to be driven by a combination of optimized conditions for photosynthesis and the absence of nutrition. Thus, the stress phase in the above-described process relies on the algae to consume the nutrients in the water to depletion, a long process that leaves many of the cells in a destructive state, resulting in a significant portion of the cells dying. This death and subsequent decay of a portion of the algae cells further results in many contaminants in the algae and water mixture.

Additionally, many of the existing processes for breaking down the cell walls of Haematococcus pluvialis cells are cumbersome and/or destructive. For example, acids are capable of destroying the cell walls of Haematococcus pluvialis cells. However, acids can also degrade the astaxanthin released from the cells. Conventional methods for milling Haematococcus pluvialis cells tend to be imprecise and can result in the introduction of oxidizing sub-processes to the astaxanthin. Too much thermochemical stress through the use of temperature and/or acids can further degrade the astaxanthin through oxidation. For this reason, the current methods of extraction and presentation, storage and processing allow too much degradation of the astaxanthin and do not in the most efficient and effective way prepare it for use.

In light of the above, there is a need in the art for an improved process for producing astaxanthin that includes improved methods and processes for producing astaxanthin-rich algae and improved methods and processes for extracting astaxanthin from the algae. There is need in the art for an improved process that provides a relatively high yield of clean, non-oxidized astaxanthin and that precludes, avoids, or reduces thermochemical stress and contamination of the astaxanthin.

BRIEF SUMMARY OF THE INVENTION

The present general inventive concept, in various example embodiments, provides a method for producing astaxanthin which incorporates a method for producing astaxanthin-rich algae and a method for extracting astaxanthin from the astaxanthin-rich algae. Various example embodiments of the present general inventive concept may be achieved by supplying an initial feedstock comprising healthy algae, water, and nutrients to an interior of a bioreactor. During a growth phase of the algae, carbon dioxide may be supplied to the feedstock, and light from a light source may be supplied to the feedstock, thereby amplifying the algae. At least a portion of the nutrients remaining after amplification of the algae may be separated from the amplified algae. During a stress phase, carbon dioxide may be supplied to the amplified algae and light from a light source may be supplied to the amplified algae, thereby promoting production of astaxanthin by the amplified algae.

In various example embodiments of the present general inventive concept, the algae is Haematococcus pluvialis. In various embodiments, additional nutrients may be supplied to the initial feedstock during the growth phase. In various embodiments, the light supplied from the light source to the feedstock during the growth phase may conform to a flashing pattern conducive to amplification of the algae. For example, in certain embodiments, the flashing pattern may comprise approximately four flashes per second. In certain embodiments, the flashing pattern may comprise approximately one hundred flashes of light per second, with each flash having a duration of approximately ten microseconds.

In various embodiments, the operation of separating at least a portion of the nutrients remaining after amplification of the algae from the amplified algae may further comprising the operations of subjecting a mixture comprising the water and nutrients of the feedstock remaining after amplification of the algae and the amplified algae to filtration to separate at least a portion of the remaining water and nutrients from the amplified algae, and supplying clean water to the filtered amplified algae. In various embodiments, the operation of subjecting the mixture to filtration may be accomplished by directing the mixture along a tangential flow filter, wherein a retentate is formed comprising the amplified algae and a permeate is formed comprising the separated portion of the remaining water and nutrients. In various embodiments, the operation of separating at least a portion of the nutrients remaining after amplification of the algae from the amplified algae may be repeated until substantially all of the nutrients remaining after amplification of the algae are separated from the amplified algae.

Various example embodiments of the present general inventive concept may be achieved by providing an attrition mill having interior surfaces and media which are substantially non-reactive to astaxanthin, supplying an amount of astaxanthin-rich algae cells and a cover to the interior of the attrition mill, and milling the astaxanthin-rich algae cells and the cover in the attrition mill to break the algae cells and release the astaxanthin to the cover. In various embodiments, the cover may limit oxidation of the released astaxanthin.

In various example embodiments of the present general inventive concept, the astaxanthin-rich algae cells may be cooled during milling. In certain embodiments, the operation of cooling the astaxanthin-rich algae cells during milling may be accomplished by cooling the attrition mill. In certain embodiments, the released astaxanthin may be further milled in the cover to reduce the average grain size of the released astaxanthin. In certain embodiments, the average grain size of the released astaxanthin is reduced to less than thirty nanometers. In certain embodiments, the average grain size of the released astaxanthin is reduced to approximately the size of a single astaxanthin molecule. In certain embodiments, the cover may be selected from the group consisting of ethanol and a hydrophobic lipid-based oil. In certain embodiments, the cover may be edible by animals. In certain embodiments, the cover may be separated from the released astaxanthin.

Additional aspects and advantages of the present general inventive concept will be set forth in part in the description which follows, and, in part, will be obvious from the description, or may be learned by practice of the present general inventive concept.

BRIEF DESCRIPTION OF THE SEVERAL VIEWS OF THE DRAWINGS

The following example embodiments are representative of example techniques and structures designed to carry out the objects of the present general inventive concept, but the present general inventive concept is not limited to these example embodiments. In the accompanying drawings and illustrations, the sizes and relative sizes, shapes, and qualities of lines, entities, and regions may be exaggerated for clarity. A wide variety of additional embodiments will be more readily understood and appreciated through the following detailed description of the example embodiments, with reference to the accompanying drawings in which.

DETAILED DESCRIPTION OF THE INVENTION

Reference will now be made to the example embodiments of the present general inventive concept, examples of which are illustrated in the accompanying drawings and illustrations. The example embodiments are described herein in order to explain the present general inventive concept by referring to the figures. The following detailed description is provided to assist the reader in gaining a comprehensive understanding of the structures and fabrication techniques described herein. Accordingly, various changes, modification, and equivalents of the structures and fabrication techniques described herein will be suggested to those of ordinary skill in the art. The progression of fabrication operations described are merely examples, however, and the sequence of operations is not limited to that set forth herein and may be changed as is known in the art, with the exception of operations necessarily occurring in a certain order. Also, description of well-known functions and constructions may be omitted for increased clarity and conciseness.

Note that spatially relative terms, such as "up," "down," "right," "left," "beneath," "below," "lower," "above,"

"upper" and the like, may be used herein for ease of description to describe one element or feature's relationship to another element(s) or feature(s) as illustrated in the figures. Spatially relative terms are intended to encompass different orientations of the device in use or operation in addition to the orientation depicted in the figures. For example, if the device in the figures is turned over or rotated, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

Figure 1:
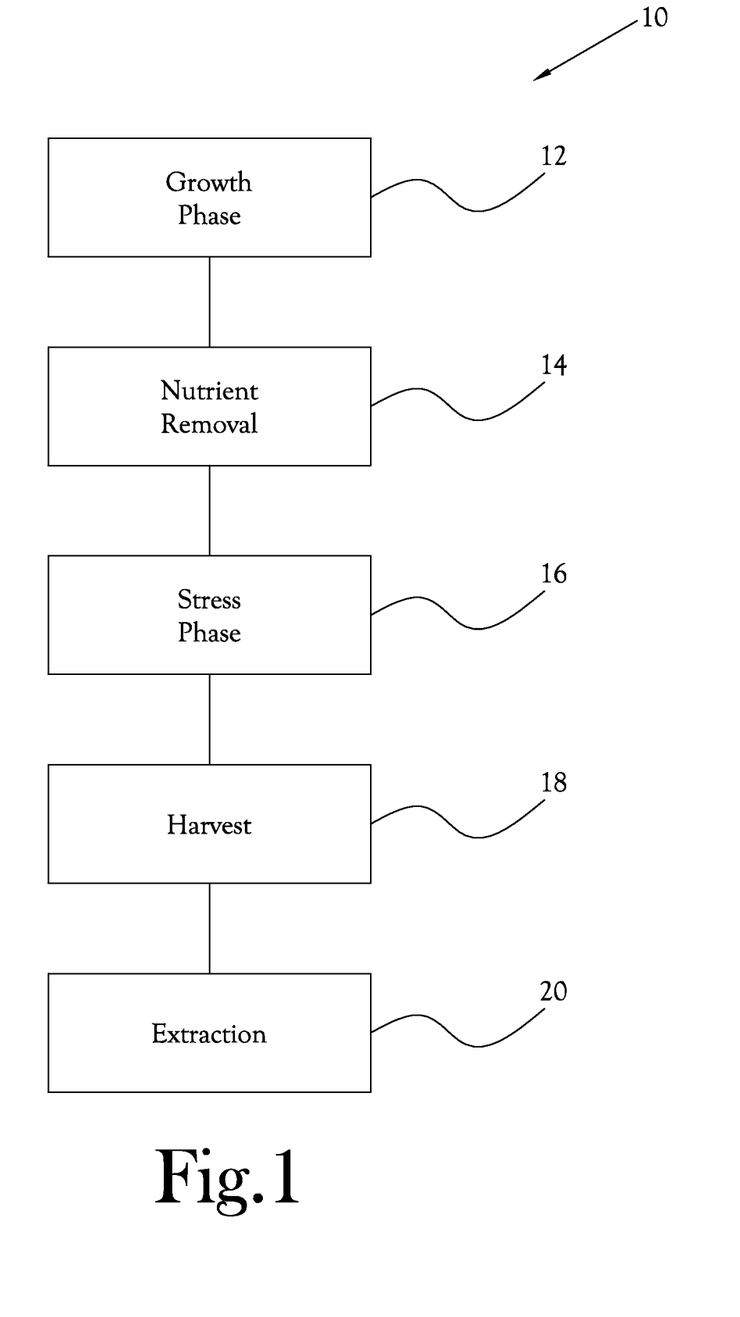
FIG. 1 is a flow chart illustrating one embodiment of a method for producing astaxanthin in accordance with several features of the present general inventive concept.

According to various examples of the present general inventive concept, an improved method for producing astaxanthin is provided. One embodiment of an improved method for producing astaxanthin, or "method" is illustrated generally at 10 in the figures. With reference to FIG. 1, in the illustrated embodiment, the method 10 includes generally a growth phase 12 in which a culture of Haematococcus pluvialis cells is grown in water containing nutrients and in conditions conducive to Haematococcus pluvialis growth. Following the growth phase 12, the nutrients are rapidly removed 14 from the Haematococcus pluvialis culture, and the Haematococcus pluvialis culture is subjected to a stress phase 16 to encourage the production of astaxanthin within the Haematococcus pluvialis cells. In this manner, a relatively high yield of healthy, astaxanthin-rich Haematococcus pluvialis cells is produced. In various embodiments, the astaxanthin-rich Haematococcus pluvialis cells are harvested 18 and subjected to an extraction process 20 to release the astaxanthin from the cells. As will be discussed further hereinbelow, the extraction process 20 is configured to produce a relatively high yield of clean, non-oxidized astaxanthin having a desirably small grain size and high surface area, as compared to prior art processes known in the art, and to limit, and in some embodiments avoid, contamination or degradation of the astaxanthin.

Figure 2:
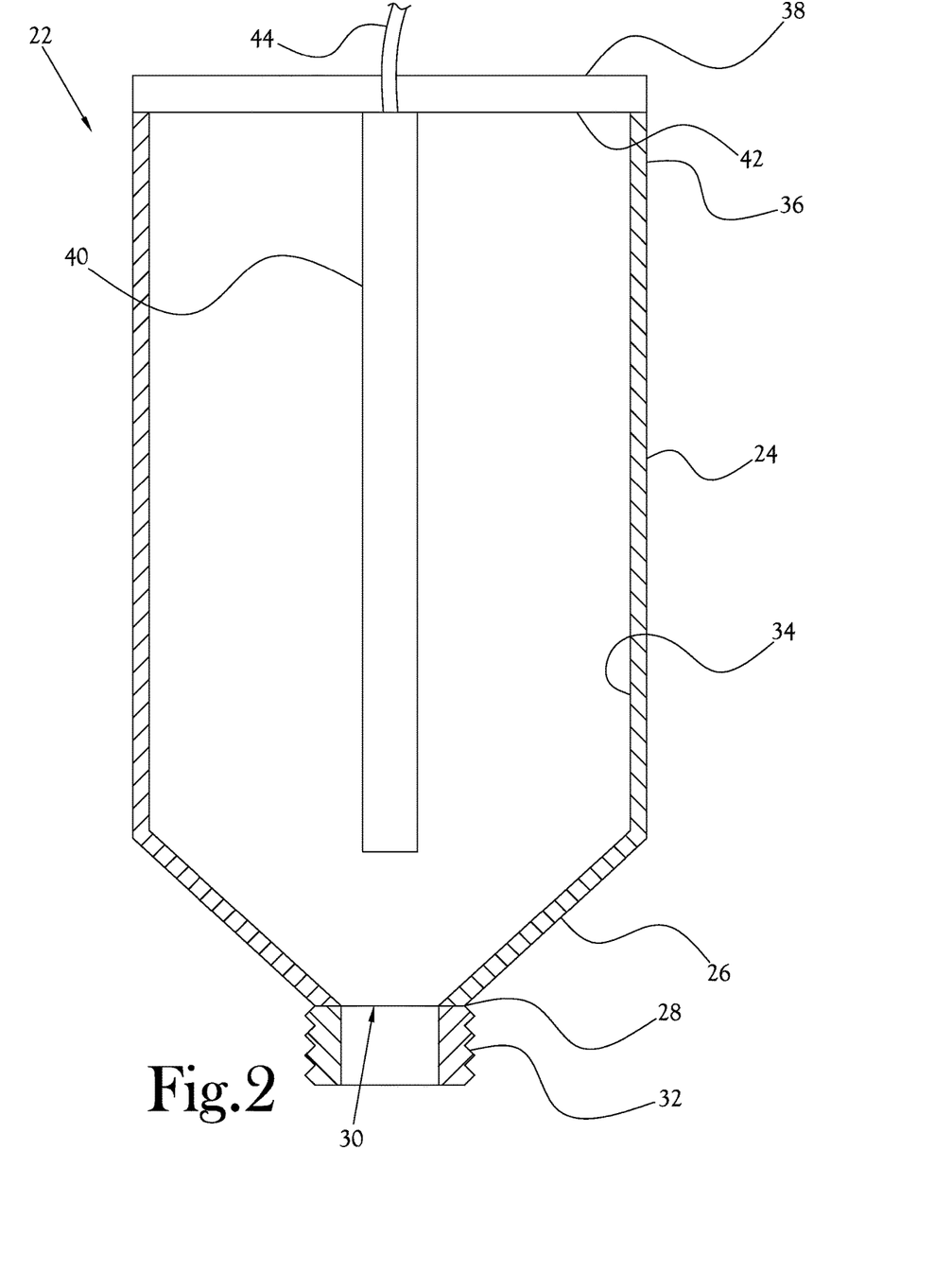
FIG. 2 is a cross-sectional side view illustrating one embodiment of a bioreactor constructed in accordance with several features of the present general inventive concept and useful in conducting the growth phase of the method.

In various embodiments of the present general inventive concept, the growth phase 12 begins with an initial setup of Haematococcus pluvialis algae for growth in one or more bioreactors 22. In various embodiments, the initial setup includes the provision of one or more bioreactors 22 suitable for growing a culture of Haematococcus pluvialis cells therein. For example, FIG. 2 is a cross-sectional view of one embodiment of a bioreactor 22 useful, for example, in growing a culture of Haematococcus pluvialis cells. With reference to FIG. 2, in one embodiment, each bioreactor 22 comprises a substantially elongate, cylindrical vessel 24, having a vertically-extending central axis and defining a frustoconical tapered portion 26 at a lower end thereof. A lower end 28 of the tapered portion 26 defines an opening 30 which is in fluid communication with a coupler 32, of the type suitable for establishing a substantially fluid tight connection with a pipe, hose, or other such conduit. Thus, a conduit having a suitable valve of the type known in the art defined along a length thereof may be secured to the coupler 32 to close the lower end 28 of the tapered portion 26, thereby establishing a substantially fluid tight volume internal of the vessel 24 for holding an amount of water or other fluid materials therein.

In certain embodiments, a valve (not shown) is provided proximate the opening 30 at the lower end 28. The valve may be adjusted between an open position and a closed position in order to selectively allow or disallow liquid to flow through the opening 30. Thus, in such embodiments, liquid received within the vessel 24 may be removed therefrom by selectively opening the valve and allowing the liquid to drain from the vessel 24. Alternatively, the valve may be closed to configure the bioreactor 22 to hold liquid therein.

In various embodiments, the bioreactor 22 defines a closed or closable upper end 36. For example, in the illustrated embodiment, a lid 38 is provided which is sized and shaped to mate with and close the upper end 36 of the vessel 24. In various embodiments, a light source 40 is provided along an interior surface 42 of the lid 38 and is configured to extend into the interior of the vessel 24. In the illustrated embodiment, the light source 40 comprises an elongate fluorescent light mounted to the lid interior surface 42 and configured such that, when the lid 38 is mated with the upper end 36 of the vessel 24, the fluorescent light extends along a central axis of the bioreactor 22. Suitable wiring 44 and other hardware of the type known to one of skill in the art is provided to supply electricity to power the light source 40 and to allow the light source 40 to be turned on and off. Thus, when the lid 38 is mated with the upper end 36 of the vessel 24, the light source 40 extends generally along a central axis of the bioreactor 22 and may be activated to provide light to the interior of the bioreactor 22.

It will be recognized that the vessel 24 may be fabricated from any of a number of substantially rigid materials known to one of skill in the art without departing from the spirit and scope of the present general inventive concept. However, in several embodiments, the vessel 24 is fabricated from one or more materials, at least one of which assists in confining light emanated from the light source 40 to an interior of the bioreactor 22. For example, in certain embodiments, the vessel 24 is fabricated from an opaque material, such as for example metal, plastic, opaque fiberglass, or the like. In certain embodiments, the vessel 24 is at least diffusely reflective of light, such that at least a portion of light from the light source 40 reaching the walls of the vessel 24 is reflected back into the vessel interior. For example, in the embodiment of FIG. 2, the vessel 24 is fabricated from a fiberglass material having a layer of white gelcoat along an interior surface 34 thereof. The white gelcoat is diffusely reflective of light striking the interior surface 34 of the vessel 24. Thus, light from the light source 40 reaching the interior surface 34 of the vessel 24 is diffusely reflected back into the interior of the vessel 24. In other embodiments, the interior surface 34 of the vessel 24 defines a mirrored surface finish of the type configured to produce specular reflection of light striking the interior surface 34 of the vessel 24. Those skilled in the art will recognize other suitable materials and configurations which may be used in fabrication of the vessel 24 without departing from the spirit and scope of the present general inventive concept.

It will further be recognized that numerous additional structures and devices exist which may be used as a bioreactor to accomplish the growth phase 12 in accordance with the present general inventive concept. For example, in one embodiment, a bioreactor is provided which comprises a single-use transparent bag having a diameter of approximately 25-30 centimeters and a height of approximately two meters. In other embodiments, one or more drums, tanks, containers, pools, ponds, or the like may be used to accomplish the initial setup of the growth phase 12 described herein.

Figure 3:
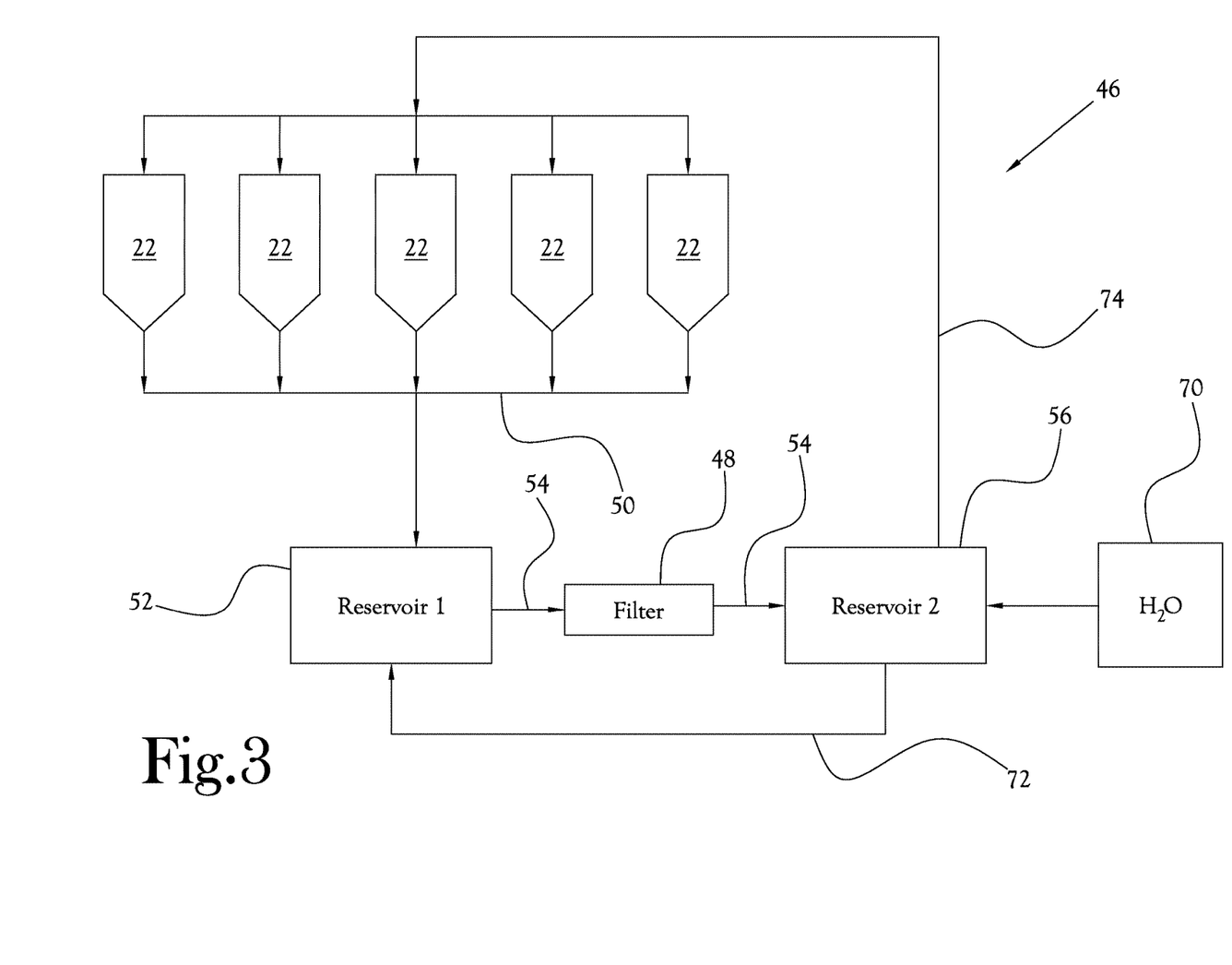
FIG. 3 is a schematic diagram illustrating one embodiment of a system constructed in accordance with several features of the present general inventive concept and useful in conducting the method.

FIG. 3 is a schematic representation of one embodiment of a system 46 which may be used to accomplish several operations of the method 10 in accordance with several features of the present general inventive concept. With reference to FIG. 3, in one embodiment, a plurality of bioreactors 22 of the type described above are provided. In the above-discussed initial setup operation of the growth phase 12, a mixture comprising water and an initial stock of Haematococcus pluvialis cells is placed within each bioreactor 22. One or more nutrients of the type known in the art, such as for example nitrates, phosphates, sodium, and silicates, are provided to the mixture within each bioreactor 22. Each mixture is exposed to an amount of light and carbon dioxide favorable for growth of the Haematococcus pluvialis algae, and each mixture is maintained at a temperature favorable for growth of the Haematococcus pluvialis algae. In this manner, each bioreactor 22 is configured to allow and promote growth of Haematococcus pluvialis algae within the bioreactor 22.

As discussed above, in various embodiments, each initial mixture of water and Haematococcus pluvialis cells is exposed to light via the light source 40 within each bioreactor 22. In one embodiment in which the interior of the vessel 24 is reflective to light, light is emitted in a 360-degree pattern outwardly from the light source 40 and reflects from the interior 34 of the vessel 24, such that the algae within each bioreactor 22 is exposed to light from a plurality of directions. In other embodiments in which the vessel 24 is fabricated from a transparent or translucent material, one or more exterior light sources may be provided outside each bioreactor 22 and configured to direct light into the interior of each vessel 24.

In various embodiments, sufficient turbulence and/or agitation is maintained within each bioreactor 22 to allow a significant portion of the algae cells within each bioreactor 22 to have at least intermittent exposure to the light within the bioreactor 22, as well as the carbon dioxide and nutrients supplied therein. For example, in the present embodiment, carbon dioxide is supplied to the water and algae mixture within each bioreactor 22 in the form of gas flow from the lower portion 26 of the bioreactor 22 to the upper portion 36 of the bioreactor 22. More specifically, in the present embodiment, a mixture of carbon dioxide and air is pumped, via an air pump and suitable conduit of the type known in the art, into an interior of the lower portion 26 of each bioreactor 22. This carbon dioxide and air mixture is allowed to *diffuse* and rise to an upper surface of the water and algae mixture within the bioreactor 22, thereby providing carbon dioxide to promote growth of the algae within the bioreactor 22 and to stabilize the pH within the bioreactor 22. This upward gas flow further serves to gently agitate the water and algae mixture within the bioreactor 22 with minimal damage to the algae, such that the algae circulates within the bioreactor 22 to expose a significant portion of the algae to the nutrients within the water, while also allowing the algae to at least intermittently receive light from the light source 40 without being shaded by adjacent algae.

It will be recognized that other devices and configurations exist which may be used to allow the algae to be exposed to the light, carbon dioxide, and nutrients supplied within each bioreactor 22. For example, in various embodiments, an impeller or other mechanical mixing device may be provided to stir or otherwise agitate the water and algae mixture within the bioreactor 22. However, it will be understood that such mixing devices should preferably be configured to result in minimal damage and/or degradation to the algae within the bioreactor 22.

Following the above-discussed setup of the bioreactors 22 containing the water, algae, and nutrients, and exposure of the contents of the bioreactors 22 to light and carbon dioxide, each bioreactor 22 is maintained within a temperature range and in conditions conducive to growth of Haematococcus pluvialis algae for a period of time sufficient to allow growth and amplification of the algae to a desired algal density of the water and algae mixture. For example, in several embodiments, each bioreactor 22 is maintained at a temperature of between approximately 20 to 36 degrees Celsius (approximately 68 to 96.8 degrees Fahrenheit) for a period of between approximately 8 to 12 days. In more discreet embodiments, each bioreactor 22 is maintained at a temperature of between approximately 22 to 34 degrees Celsius (approximately 71.6 to 93.2 degrees Fahrenheit), and in even more discreet embodiments, between approximately 25 to 28 degrees Celsius (approximately 77 to 82.4 degrees Fahrenheit), for a period of between approximately 8 to 12 days. In even more discreet embodiments, each bioreactor 22 is maintained at a temperature of approximately 28 degrees Celsius (approximately 82.4 degrees Fahrenheit) for a period of between approximately 8 to 12 days. Throughout this time, additional nutrients are optionally added to the interior of each bioreactor 22 to replace any nutrients consumed by the algae growing therein, and to maintain a supply of suitable nutrients within each bioreactor 22 for further algal growth. To the extent water is lost from one or more bioreactors 22 due to evaporation or other losses, additional water is optionally added to maintain the amount of water and algae mixture within each bioreactor 22. Additional adjustments to the water and algae mixture may optionally be made, via water additives or other means known in the art, in order to maintain suitable pH, water chemistry, and water quality within each bioreactor 22 conducive to Haematococcus pluvialis algal growth.

In some embodiments, the above-discussed mixture of carbon dioxide and air is continually pumped into each bioreactor 22 as discussed above throughout the growth phase 12, such that the water and algae mixture within each bioreactor 22 is continually supplied with carbon dioxide. In other embodiments, the mixture of carbon dioxide and air is intermittently pumped into each bioreactor 22 throughout the growth phase 12, such that the overall amount of carbon dioxide within the water and algae mixture within the bioreactor 22 is maintained within an acceptable range conducive to growth of the Haematococcus pluvialis algae. Likewise, in some embodiments, each light source 40 of each bioreactor 22 is configured to continually direct light to the water and algae mixture within the bioreactor 22 throughout the growth phase 12. In other embodiments, each light source 40 of each bioreactor 22 is configured to direct light intermittently to the water and algae mixture within the bioreactor 22, for example to mimic the day and night cycle of natural sunlight, such that the overall amount of light supplied to the water and algae mixture within each bioreactor 22 is maintained at a level conducive to growth of the Haematococcus pluvialis algae. In certain embodiments, each light source 40 is configured to emit light in a flashing pattern generally conducive to growth and photosynthesis of the Haematococcus pluvialis algae. For example, in one embodiment, the light source 40 is a light-emitting diode (LED) light source configured to emit flashes of light in a pattern of very short, successive flashes. More specifically, in one embodiment, the light source 40 is configured to emit approximately four (4) flashes of light per second, with each flash of light comprising light in the wavelength range of between approximately 700-800 nanometers. In another embodiment, the light source 40 is configured to emit approximately one hundred (100) flashes of light per second, with each flash of light having a flash duration of approximately 10 microseconds. Those of skill in the art will recognize other patterns of flashing or other intermittent light which may be used to accomplish the growth phase 12 without departing from the spirit and scope of the present general inventive concept.

It will be recognized that the above-described maintenance of the bioreactors 22 during the growth phase 12 results generally in encouragement of the quantity of Haematococcus pluvialis algae within each bioreactor 22 to amplify to an algal density greater than that of the feedstock of algae initially supplied to the bioreactor 22. In several embodiments, during the growth phase 12, the Haematococcus pluvialis algae within each bioreactor 22 is permitted to amplify to an algal density at or approaching the maximum algal density for which conditions conducive to growth of the Haematococcus pluvialis algae may be maintained through the above-described processes. In other embodiments, the Haematococcus pluvialis algae within each bioreactor 22 is permitted to amplify to an algal density at or approaching an upper limit whereupon further growth of the Haematococcus pluvialis algae would likely result in death or degradation of a significant portion of the Haematococcus pluvialis algae within the bioreactor 22. In still other embodiments, the Haematococcus pluvialis algae within each bioreactor 22 is permitted to amplify to a target or desired algal density.

Upon completion of the above-discussed growth phase 12, each bioreactor 22 contains a mixture comprising water, nutrients, and an amplified quantity of Haematococcus pluvialis algae. Following the growth phase 12, this mixture is subjected to a nutrient removal operation 14 in order to rapidly separate a significant portion, and in some embodiments an amount approaching substantially all, of the supplied nutrients from the algae. In various embodiments, the nutrient removal operation 14 is accomplished via filtration of the contents of the bioreactors 22 by a filter device 48 in order to separate the Haematococcus pluvialis algae from the water containing the nutrients. For example, in the system 46 illustrated in FIG. 3, each coupler 32 at each lower end opening 30 of each bioreactor 22 is connected, via a first set of pipes 50, to a first processing reservoir 52 which is sized to hold the collective contents of each bioreactor 22. In this embodiment, upon completion of the growth phase 12, the contents of each bioreactor 22 is transferred to the first processing reservoir 52. Such contents are then directed via a second set of pipes 54 through the filter device 48 and into a second processing reservoir 56.

Figure 4:
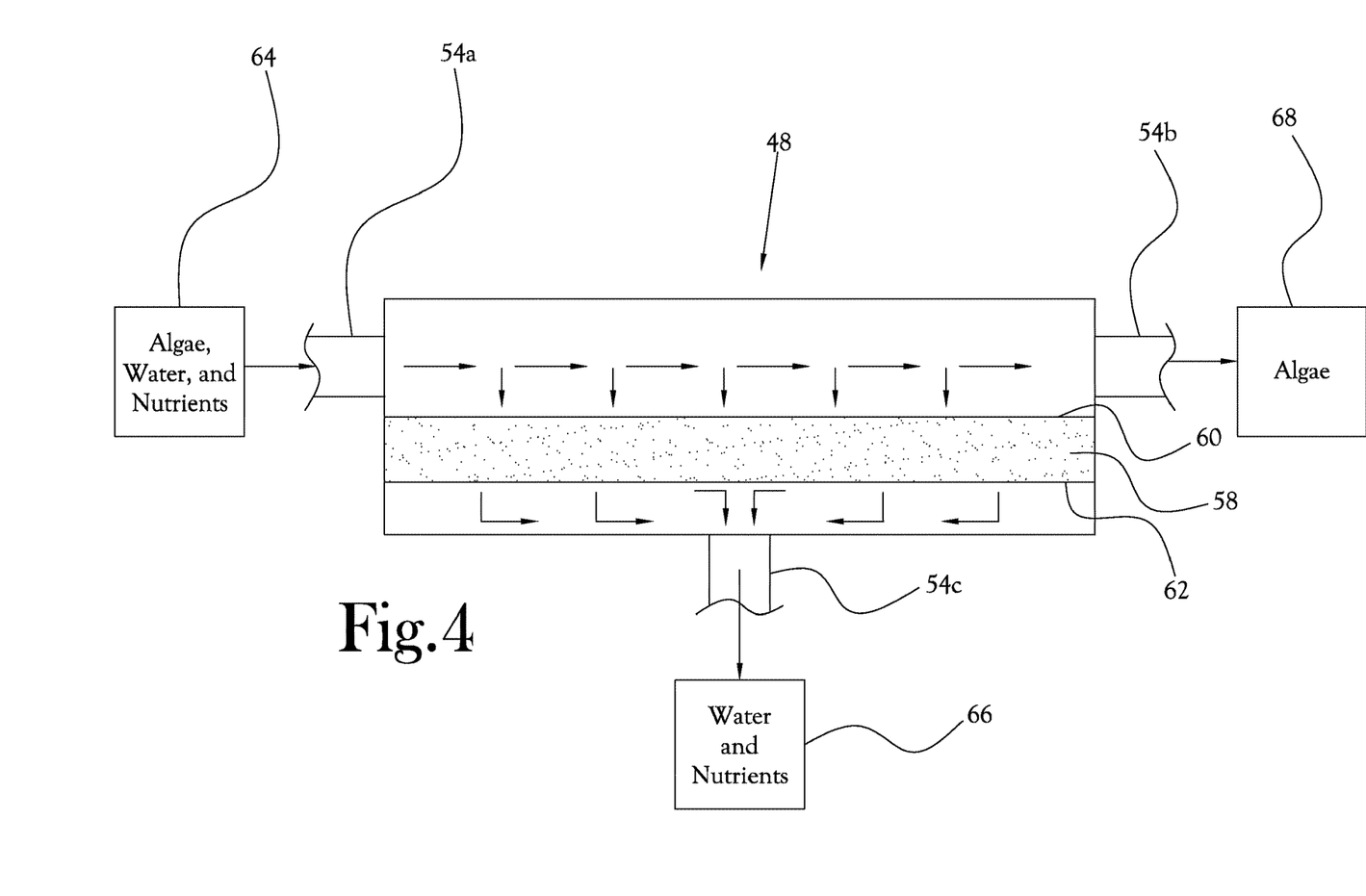
FIG. 4 is a cross-sectional side view illustrating one embodiment of a filter constructed in accordance with several features of the present general inventive concept and useful in performing the nutrient removal operation of the method.

In several embodiments, the filter device 48 is of a type commonly known as a "crossflow filter" or "tangential flow filter." One embodiment of such a filter 48 is illustrated in FIG. 4. With reference to FIG. 4, in one embodiment, the filter 48 comprises generally a filtration membrane 58 having a retentate side 60 and a permeate side 62, and defining a plurality of pores which are sized to disallow Haematococcus pluvialis algae cells to pass through the membrane 58, but to allow at least a portion of the water containing the nutrients to pass through the membrane 58. For example, in one embodiment each of the plurality of pores is approximately less than or equal to ten microns. The filter 48 is configured such that the mixture of algae, water, and nutrients 64 is directed tangentially across the retentate side 60 of the membrane 58. As the mixture of algae, water, and nutrients 64 travels through the filter 48, positive pressure is maintained on the retentate side 60 relative to the permeate side 62. Thus, a portion of the water containing the nutrients passes through the membrane 58 and forms a permeate 66 of the filter 48. The algae and the portion of water and nutrients which do not pass through the membrane 58 form a retentate 68 of the filter 48.

Referring to FIGS. 3 and 4, in the illustrated embodiment, the mixture of algae, water, and nutrients 64 is directed from the first processing reservoir 52, through an input pipe 54a, to a retentate side 60 of the interior of the filter 48. The mixture 64 is then allowed to flow substantially tangential to the retentate side 60 of the membrane 58, whereupon the permeate 66 flows through the membrane 58 as discussed above and is thus separated from the retentate 68. In one embodiment, the mixture 64 flowing tangential to the retentate side 60 is maintained at relatively low pressure, such as for example less than one atmosphere of pressure. The retentate 68, comprising the algae and the portion of water and nutrients which do not pass through the membrane 58, is directed through a first output pipe 54b from the filter 48 to the second processing reservoir 56. The permeate 66, comprising the portion of the water containing the nutrients which passes through the membrane 58, is directed through a second output pipe 54c to an output of the filter 48. In various embodiments, the permeate 66 is discarded as waste. In other embodiments, the permeate 66 may be retained for use in subsequent iterations of the above-discussed growth phase 12.

It will be recognized that, due to the removal by the filter 48 of the portion of the water containing nutrients forming the permeate 66, the retentate 68 of the filter 48 thus contains a higher concentration of algae than the mixture 64 of algae, water, and nutrients fed into the filter 48 from the first processing reservoir 52. Thus, in various embodiments, once the retentate 68 is passed through the filter 48 and received into the second processing reservoir 56, additional clean water is added to the algae via a water source 70. Thus, a mixture is formed in the second processing reservoir 56 comprising water, the amplified quantity of Haematococcus pluvialis algae, and a significantly reduced amount of the above-discussed nutrients.

It will be recognized that the amount of water and nutrients removed from the mixture 64 as permeate 66 as a result of passing the mixture 64 through the filter 48 is dependent upon several factors, including, but not limited to, the permeability of the membrane 58, the surface area and length of the flow path across the retentate side 60 of the membrane 58, the pressure differential maintained between the retentate side 60 and permeate side 62 of the membrane 58, and the rate of flow of the mixture 64 through the filter 48, among other factors. In this regard, in one embodiment, the filter 48 is configured to allow the removal of a significant portion of the water and nutrients from the mixture 64 in a single pass through the filter 48. In this embodiment, the nutrient removal operation 14 may be completed by performing a single pass of the mixture 64 through the filter 48, followed by a single iteration of adding clean water in the second processing reservoir 56 in order to form a mixture of algae and water absent a significant portion of the supplied nutrients. In other embodiments, the nutrient removal operation 14 may comprise multiple iterations of alternating filtration and water addition operations in order to form the mixture of algae and water absent the significant portion of the supplied nutrients. For example, in the embodiment of FIG. 3, the second processing reservoir 56 is connected, via a third set of pipes 72, to the first processing reservoir 52. Thus, once the initial mixture 64 of algae, water, and nutrients is passed through the filter 48 a first time to remove the portion of water containing the nutrients, and once clean water is added to the algae in the second processing reservoir 56, the resultant mixture of water, algae, and the reduced quantity of nutrients may be directed back to the first processing reservoir 52, whereupon the mixture may again be passed through the filter 48 in order to remove additional water and nutrients from the mixture. Additional clean water may then be added to further dilute the nutrients within the mixture following the second pass through the filter 48. In various embodiments, this process of iterative filtration and water addition may be repeated until a desired portion of the supplied nutrients is removed from the mixture, thereby completing the nutrient removal operation 14. In certain embodiments, the process of iterative filtration and water addition is repeated until removal of approximately 90% or more of the nutrients and contaminants from the water and algae mixture is achieved, and in certain more discreet embodiments, until approximately 92% or more of the nutrients and contaminants are removed.

Following the above-discussed nutrient removal operation 14, the mixture of algae and water is subjected to a stress phase 16, in which the algae is maintained in a relatively low-nutrient environment in conditions which are otherwise conducive to photosynthesis and growth of the Haematococcus pluvialis algae. For example, with further reference to FIG. 3, in one embodiment, following the nutrient removal operation 14, the mixture of algae and water is returned to the various bioreactors 22 via a fourth set of pipes 74. Similarly to the above-described growth phase 12, the mixture of water and Haematococcus pluvialis cells is exposed to light via the light sources 40 within the bioreactors 22, and is provided with a supply of carbon dioxide via a mixture of carbon dioxide and air pumped into each bioreactor 22 as discussed above. In one embodiment, during the stress phase 16, the Haematococcus pluvialis algae within the bioreactors 22 is exposed to light levels in the range of 100-800 micromoles per square meter per second or more, and temperatures in the range of between approximately 20 to 36 degrees Celsius (approximately 68 to 96.8 degrees Fahrenheit) are maintained. In this nutrient depleted but photosynthesis conducive environment, the Haematococcus pluvialis algae within the bioreactors 22 is encouraged to produce astaxanthin within the algae cells.

It will be recognized that the above-described processes throughout the growth phase 12, the nutrient removal phase 14, and the stress phase 16 are configured to result in minimal damage or degradation to the cells of the Haematococcus pluvialis algae within the mixture. For example, during the nutrient removal phase 14, the above-discussed filter 48 is configured to maintain flow of the algae cells across the membrane 58 and to discourage the algae cells from becoming lodged in the membrane 58, thereby damaging the cells. Furthermore, the above-discussed nutrient removal phase 14 allows for rapid removal of nutrients and other contaminants from the mixture of water and algae, thereby minimizing the amount of time the algae is deprived of water and/or nutrients, and limiting the amount of time the algae is exposed to contaminants, prior to the stress phase 16. Thus, following the above-discussed nutrient removal phase 14, the mixture of algae and water subjected to the stress phase 16 includes a relatively high quantity of healthy algae cells with a minimal amount of dead or dying algae cells or other contaminants. Accordingly, during the stress phase 16, a relatively high yield of astaxanthin is produced by the healthy algae as compared to various prior art processes. For example, in various embodiments, the above-described stress phase 16 results in the production of an amount of astaxanthin by the Haematococcus pluvialis algae in excess of 1.5% of the dry weight of the Haematococcus pluvialis algae. In certain more discreet embodiments, the above-described stress phase 16 results in the production of an amount of astaxanthin by the Haematococcus pluvialis algae approaching, or approximately equal to, four percent (4%) of the dry weight of the Haematococcus pluvialis algae. Thus, those of skill in the art will recognize that an improved method for the production of astaxanthin-rich algae is provided.

With reference again to FIG. 3, it will be recognized that various additional devices may be provided in the system 46 in various configurations to facilitate movement of the algae, water, and nutrient mixtures between the bioreactors 22, the first and second processing reservoirs 52, 56, and the filter 48, and to facilitate containment of the algae, water, and nutrient mixtures within the bioreactors 22 and the reservoirs 52, 56. For example, in several embodiments, suitable valves (not shown) are provided proximate leading ends of each of the first, second, third, and fourth sets of pipes 50, 54, 72, 74 and are configured to regulate flow through the respective pipes. The various valves may be adjusted between open and closed positions such that flow through each of the pipes 50, 54, 72, 74 may be allowed or disallowed. Additionally, in various embodiments, a drive mechanism is provided to drive flow of the algae, water, and nutrient mixtures through the various pipes 50, 54, 72, 74 when the valves associated with such pipes are in an open position. For example, in the embodiment of FIG. 3, each of the bioreactors 22 and the reservoirs 52, 56 defines a substantially airtight interior, and a source of pressurized air is provided in fluid communication with the interiors of each of the bioreactors 22 and the reservoirs 52, 56. Thus, pressurized air may be selectively introduced to at least one of the bioreactors 22 or the reservoirs 52, 56 to drive flow of the algae, water, and nutrient mixtures through the pipes 50, 54, 72, 74 associated therewith. For example, in the illustrated embodiment, an air pump is provided in fluid communication with the interior of the first processing reservoir 52. As discussed above, each of the bioreactors 22 is configured such that, upon opening the valves associated with the first set of pipes 50, the mixture of algae, water, and nutrients may drain from the bioreactors 22 into the first processing reservoir 52. Thereafter, the valves associated with the first set of pipes 50 may be closed, and the valves associated with the second set of pipes 54 may be opened, such that flow of the algae, water, and nutrient mixture is allowed through only the second set of pipes 54. Air may then be pumped into the first processing reservoir 52 in order to urge the algae, water, and nutrient mixture through the second set of pipes 54, thus moving the algae, water, and nutrient mixture through the filter 48. Likewise, once the filtered algae and water is received within the second processing reservoir 56 and the additional water added thereto, the valves associated with the second set of pipes 54 may be closed, and the valves associated with the third or the fourth set of pipes 72, 74 may be opened to allow the flow of algae and water back to the first processing reservoir 52 or to the bioreactors 22, respectively. Thereafter, air may be pumped into the second processing reservoir 56 in order to urge the algae and water mixture through either the third or fourth set of pipes 72, 74, thus moving the algae and water mixture to the desired destination.

Those skilled in the art will recognize other devices which are suitable for use in directing the algae, water, and nutrients throughout the system 46, and such other devices may be used without departing from the spirit and scope of the present general inventive concept. In various embodiments, suitable pumps are provided to facilitate transfer of the water and algae mixture to the various stations throughout the system 46. For example, in one embodiment, a plurality of peristaltic pumps are provided throughout the system 46 to pump the water and algae mixture to the various stations therein.

Figure 5:
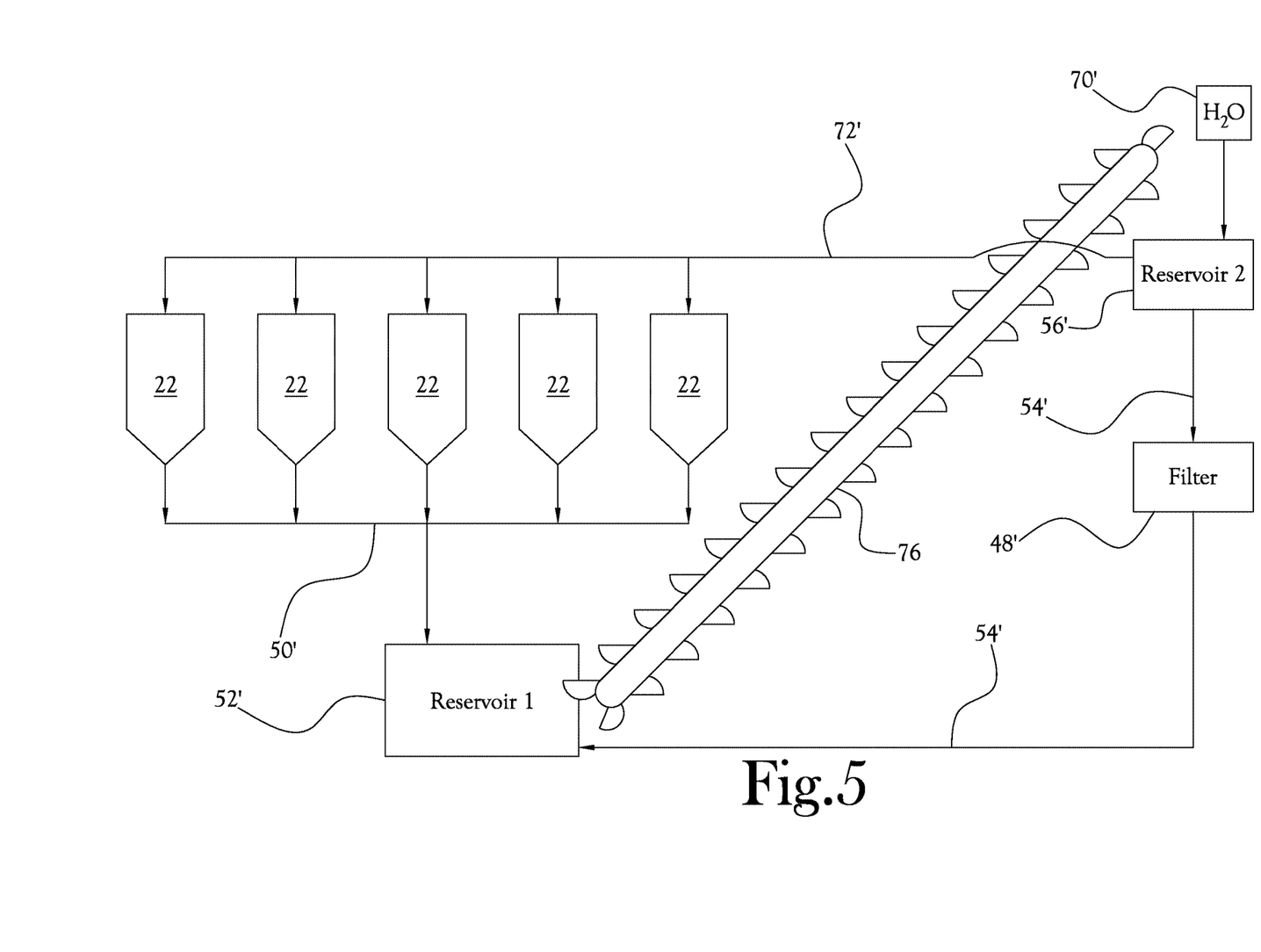
FIG. 5 is a schematic diagram illustrating another embodiment of a system constructed in accordance with several features of the present general inventive concept and useful in conducting the method.

FIG. 5 illustrates another embodiment of a system 46'. In the embodiment of FIG. 5, the first processing reservoir 52' is situated at a lower hydraulic gradient in relation to the bioreactors 22, such that the bioreactors 22 are collectively configured to drain into the first processing reservoir 52' upon opening the necessary valves to allow the contents of the bioreactors 22 to flow through their respective lower end openings 30 and through the first set of pipes 50'. The second processing reservoir 56' is situated at a higher hydraulic gradient in relation to both the bioreactors 22 and the first processing reservoir 52'. In this embodiment, a conveyor 76, such as for example a bucket conveyor or the like, is provided in communication with the first and second processing reservoirs 52', 56', such that, during the nutrient removal phase 14, the conveyor 76 may receive the mixture of water, algae, and nutrients from the first processing reservoir 52' and transfer it to the second processing reservoir 56'. A second set of pipes 54' is in communication with a lower end of the second processing reservoir 56' and is configured, upon opening of suitable valves associated therewith, to allow the contents of the second processing reservoir 56' to drain therefrom and to direct such contents through the filter 48' before directing the filtered contents back to the first processing reservoir 52'. Thereafter, the conveyor 76 may return the filtered contents to the second processing reservoir 56' for addition of clean water thereto via the water source 70'. A third set of pipes 72' is in communication with the lower end of the second processing reservoir 56' and is configured, upon opening of suitable valves associated therewith, to allow the contents of the second processing reservoir 56' to drain therefrom and to direct such contents back to the bioreactors 22. Thus, in the embodiment, of FIG. 5, transfer of the mixed water, algae, and nutrients to and from each of the various stations in the system 46' throughout the growth phase 12, nutrient removal phase 14, and stress phase 16 may be accomplished solely via the conveyor 76, and in conjunction with gravitational forces acting upon the mixture.

Referring again to FIG. 1, upon completion of the stress phase 16, a mixture comprising water and astaxanthin-rich algae is produced. Thereafter, the astaxanthin-rich algae may be harvested 18. In various embodiments, the harvest operation 18 includes separation of the astaxanthin-rich algae from at least a significant portion of the water in the mixture. For example, in certain embodiments, upon completion of the stress phase 16, the mixture comprising water and astaxanthin-rich algae is transferred from the bioreactors 22 to the first processing reservoir 52, whereupon the mixture is passed at least once, and in some embodiments multiple times, through the filter 48. Similarly to the above-discussed nutrient removal operation 14, upon passing the mixture through the filter 48, a significant portion of the water in the mixture passes through the membrane 58 and exits as permeate through the second output pipe 54c to an output of the filter 48, while the astaxanthin-rich algae travels along the retentate side of the membrane 58 and exits as retentate through the first output pipe 54b. In other embodiments, upon completion of the stress phase 16, the mixture comprising water and astaxanthin-rich algae is filtered through a filter press in order to remove a significant portion of the water within the mixture. In still other embodiments, the mixture comprising water and astaxanthin-rich algae is moved to a centrifuge, whereupon the mixture is subject to centripetal acceleration in order to separate the astaxanthin-rich algae from the water. In each of these embodiments, a concentrate comprising astaxanthin-rich algae is produced.

Pursuant to several features of the present general inventive concept, an extraction method 20 is provided which is configured to allow the release and size reduction of nutrient particles, such as for example astaxanthin or other nutrients, from cells of a biomass rich in the nutrient, such as for example the above-discussed algae cells, while limiting, and in some embodiments altogether limiting, oxidation and other contamination which would decrease the effectiveness of the nutrient for use in food products and other applications. The extraction method 20 may be performed, for example, to release at least a significant portion of the astaxanthin from the algae cells in the above-discussed concentrate, or to release other nutrients from cells in a biomass.

Figure 6:
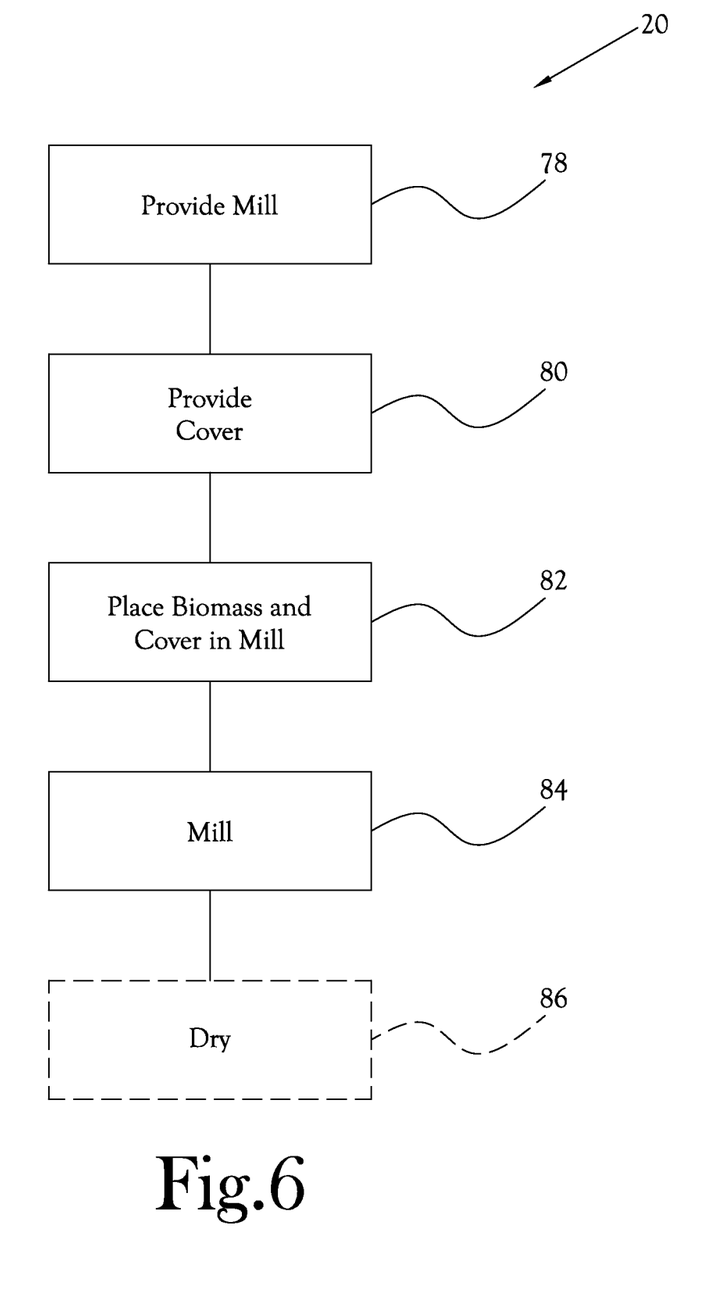
FIG. 6 is a flow chart illustrating one embodiment of a method for extracting astaxanthin from astaxanthin-rich algae cells in accordance with several features of the present general inventive concept.

FIG. 6 illustrates one embodiment of an extraction method 20 in accordance with several features of the present general inventive concept. With reference to FIG. 6, in an initial operation, a mill is provided 78 having internal milling and containment surfaces fabricated from a material which is substantially non-reactive to the nutrient such that a nutrient-rich biomass, such as the above-discussed astaxanthin-rich algae concentrate, may be contained and milled within the mill with limited, and preferably no, contact with surfaces other than the non-reactive surfaces within the mill. For example, in one embodiment, an attrition mill is provided 78 of the type comprising a vessel having a generally annular interior, a shaft extending along a central axis of the vessel, a plurality of paddles extending orthogonally from the shaft, and a plurality of media comprising balls of ceramic or other substantially hard material, the mill being configured such that the shaft and associated paddles may be rotatably driven about the central axis within the vessel to agitate the media therein. The shaft and associated paddles are preferably capable of being driven at relatively high revolutions per minute ("RPM"), i.e., approximately 50-800 RPM in various embodiments. In several embodiments, each of the shaft, paddles, and interior surfaces of the vessel are coated with a non-reactive coating, such as for example silicon nitride, polytetrafluoroethylene, or the like. In several embodiments, the media comprise zirconia and alumina materials, and are sized approximately 3 millimeters. It will be understood that other types of grinding and milling apparatus defining other configurations of milling and containment surfaces may be employed without departing from the spirit and scope of the present invention.

In various embodiments, a nutrient-rich biomass is provided. In the illustrated embodiment, the nutrient-rich biomass provided for use in the method 20 is the above-discussed astaxanthin-rich algae concentrate. For the sake of convenience herein, the terms "nutrient-rich biomass," "biomass," "astaxanthin-rich algae concentrate," "algae concentrate," and "concentrate" may be used or referred to interchangeably in reference to the nutrient-rich biomass provided for use in the method 20. However, it will be recognized that numerous other types of nutrient-rich materials may be provided for use in the method 20 without departing from the spirit and scope of the present general inventive concept. For example, in various embodiments, a biomass comprising cells rich in astaxanthin may be provided for use in the method 20 described herein. More specifically, in certain embodiments, a biomass comprising algae, yeast, or other biomaterials rich in astaxanthin may be provided, and in certain more discreet embodiments, a biomass comprising Haematococcus pluvialis algae and/or *Phaffia rhodozyma* yeast may be provided. In other embodiments, a biomass rich in one or more other nutrients may be provided. For example, in various other embodiments, a biomass comprising cells rich in omega 3 fatty acids, such as for example eicosapentaenoic acid (EPA) and/or docosahexaenoic acid (DHA), may be provided. More specifically, in certain embodiments, a biomass comprising algae, yeast, bacteria, and/or other organisms rich in omega 3 fatty acids may be provided, and in certain more discreet embodiments, a biomass may be provided comprising organisms selected from the group consisting of *Phaedactylum tricornutum, Spirulina, Chlorella, Nannochloropsis, Monodus subterraneus, Crypthecodinium cohnii, Schizochytrium, Thraustochytrium aggregatum*, and *Ulkenia* sp. In other embodiments, a biomass comprising cells rich in other types of proteins and/or amino acids may be provided. Other types of nutrients and nutrient-rich biomass materials will be recognized by one of skill in the art.

In another operation of the present embodiment, an inert cover is provided 80. The cover is generally selected to be a material suitable to limit exposure of the nutrient within the nutrient-rich biomass to oxygen and other reactants in the atmosphere during the extraction process 20. For example, in one embodiment, the cover is a measure of ethanol sufficient to substantially coat and suspend the above-discussed astaxanthin-rich algae concentrate. In other embodiments, the cover is a measure of hydrophobic, lipid-based oil of the type derived from animal or vegetable sources. In certain more discreet embodiments, the cover is selected from the group consisting of olive oil, sunflower oil, fish oil, vegetable oil, ethanol, and combinations thereof. In other embodiments, the cover is an inert gas, such as for example nitrogen, argon, etc.

In the illustrated embodiment, the astaxanthin-rich biomass and cover are combined and introduced into the mill. In the illustrated embodiment, combination of the astaxanthin-rich algae concentrate with the cover and introduction of the combination thereof into the mill occurs simultaneously as both the concentrate and the cover are placed 82 into the attrition mill. However, it will be understood that, depending upon the type of cover, the specific type of mill provided 78 and the procedure for loading items to be milled therein, the chemically reactive nature of the nutrient within the biomass and the need to protect the nutrient from reacting with atmospheric contaminants may require combination of the biomass with the cover at a time other than the time at which the biomass and cover are loaded into the mill. To this effect, in other embodiments, the biomass and cover are combined and then the combination thereof is introduced into the mill. For example, and with reference again to FIG. 3, in one embodiment, following the above-discussed stress phase 16, and after the water is removed from the mixture comprising water and astaxanthin-rich algae by the filter 48, the astaxanthin-rich algae concentrate is directed to the second processing reservoir 56. In this embodiment, the cover is added to the astaxanthin-rich algae concentrate within the second processing reservoir 56, whereupon the combination thereof is introduced into the mill. In yet another embodiment, the astaxanthin-rich algae concentrate and cover are first introduced into the mill separately, and then combined within the mill.

In an optional step, additional ingredients may be added 88 to the mill for milling and/or mixing with the nutrient-rich biomass and the cover. For example, in various embodiments in which an astaxanthin-rich biomass is provided, the additional ingredient is an ingredient comprising at least one omega 3 fatty acid, such as eicosapentaenoic acid (EPA) and/or docosahexaenoic acid (DHA). For example, in several embodiments, a measure of at least one additional biomass comprising algae and/or bacteria of the type rich in eicosapentaenoic acid (EPA) and/or docosahexaenoic acid (DHA) is added 88 to the mill. Those of skill in the art will recognize other ingredients which may be added without departing from the spirit and scope of the present general inventive concept.

Following the combination of the nutrient-rich biomass with the cover and placing thereof into the mill 82, and following the above-discussed optional addition of one or more additional ingredients 88, the mill is activated 84, whereupon the contents of the mill are milled to break open the cells of the biomass, release the nutrient therefrom, and reduce the average particle size of the released nutrient under the cover of the cover. It will be recognized that the above-discussed non-reactive milling surfaces and containment surfaces of the mill discourage grinding-based or attrition-based contamination of the nutrient during milling 84. It will further be recognized that the cover discourages oxidation or other atmospheric-based contamination of the nutrient during milling 84. In an embodiment in which an attrition mill is provided, the attrition milling 84 of the released nutrient encourages diminution of the released nutrient into particulates wherein the average grain size of the released astaxanthin is reduced to a very fine particle size. For example, in various embodiments in which the provided nutrient-rich biomass is the above-discussed astaxanthin-rich algae concentrate, the attrition milling 84 of the released astaxanthin encourages diminution of the released astaxanthin into particulates wherein the average grain size of the released astaxanthin is less than three microns in one embodiment, less than 35 nanometers in another embodiment, and less than 30 nanometers in another embodiment. It will be recognized that, in some embodiments, achievement of milling of the released astaxanthin to a particle size approximately equal to a single astaxanthin molecule may be achieved.

In various embodiments, the nutrient within the attrition mill is maintained at a relatively cool temperature in order to further discourage oxidation of the released nutrient during milling 84. For example, in certain embodiments, the provided attrition mill is water-cooled throughout the milling operation 84. It will be understood that such cool milling of the above-discussed astaxanthin-rich algae concentrate results in speedier and more efficient diminution of the released astaxanthin, and furthermore results in easier reduction of the average grain size of the released astaxanthin to a very fine particle size while simultaneously limiting the above-discussed oxidation. However, it will be understood that such cool milling of the nutrient-rich biomass is not necessary to accomplish the extraction method 20 in accordance with the present general inventive concept.

During the above-discussed milling operation 84, a slurry is produced comprising byproduct of the milled biomass, nutrient particulates, any optionally added additional ingredients, and in embodiments in which a liquid cover is used, the cover. In various embodiments, upon completion of the milling operation 84, the slurry may be removed and utilized by an end user, or packaged for subsequent use by an end user. For example, in certain embodiments in which the nutrient is astaxanthin, the cover is a material which is generally edible by fish, livestock, or other animals. In such embodiments, upon completion of the milling operation 84, the slurry may be removed and packaged for further use in, for example, marine or agriculture feed products or the like.

In other embodiments, the slurry may be optionally dried 86 to remove substantially all of the cover. For example, in one embodiment in which the cover is liquid ethanol, upon completion of the milling operation 84, the slurry is transferred to a vacuum dryer, whereupon the ethanol is evaporatively removed from the slurry to form a granular product comprising the above-discussed astaxanthin particulates and byproducts of the milled biomass.

From the foregoing description, it will be recognized by one of skill in the art that improved methods and apparatus for producing astaxanthin have been provided, the method including an improved process and method for producing astaxanthin-rich algae cells, as well as an improved process and method for extracting nutrients, such as astaxanthin, omega 3 fatty acids, or the like, from a biomass, such as algae cells. Numerous advantages of the present general inventive concept will be recognized by one of ordinary skill in the art. For example, the improved processes and methods disclosed herein provide for rapid and relatively high-yield production of astaxanthin-rich algae cells from growth to the stress stage as compared to various prior art processes. The improved processes and methods disclosed herein further provide for very high turbulence during the growth phase 12 in order to keep the algae cells circulating in the light from the light source 40. The improved processes and methods disclosed herein, and the systems and apparatus disclosed herein, allow for precise control of the water quality and content, temperature, and carbon dioxide content throughout the growth phase 12 and other operations described herein. Accordingly, more healthy astaxanthin-rich algae may be produced having a greater production of astaxanthin per algal cell as compared to prior art methods and processes. It will further be recognized that the improved processes and methods disclosed herein provide for the speedy and economical extraction and reduction of astaxanthin from astaxanthin-rich algae cells, with limited, and in some embodiments substantially no, oxidation or other contamination of the astaxanthin produced.

It is noted that the simplified diagrams and drawings do not illustrate all the various connections and assemblies of the various components, however, those skilled in the art will understand how to implement such connections and assemblies, based on the illustrated components, figures, and descriptions provided herein, using sound engineering judgment. Numerous variations, modifications, and additional embodiments are possible, and accordingly, all such variations, modifications, and embodiments are to be regarded as being within the spirit and scope of the present general inventive concept. For example, regardless of the content of any portion of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated.

While the present general inventive concept has been illustrated by description of several example embodiments, and while the illustrative embodiments have been described in detail, it is not the intention of the applicant to restrict or in any way limit the scope of the general inventive concept to such descriptions and illustrations. Instead, the descriptions, drawings, and claims herein are to be regarded as illustrative in nature, and not as restrictive, and additional embodiments will readily appear to those skilled in the art upon reading the above description and drawings. Additional modifications will readily appear to those skilled in the art. Accordingly, departures may be made from such details without departing from the spirit or scope of applicant's general inventive concept.

Having thus described the aforementioned invention, what is claimed is:

1. A method for extracting a nutrient from nutrient-rich cells comprising:
    combining a nutrient-rich cell biomass with ethanol under an inert gas in an interior of an attrition mill;
    milling the nutrient-rich cell biomass in the ethanol and under the inert gas in the attrition mill;
    breaking nutrient-rich cells of the nutrient-rich cell biomass; and
    releasing a nutrient from the nutrient-rich cells to the ethanol,
    where the ethanol and the inert gas limit oxidation of the nutrient, and
    where the milling reduces the average grain size of the nutrient to less than three microns.

2. The method of claim 1 wherein the nutrient is selected from the group consisting of astaxanthin, eicosapentaenoic acid, and docosahexaenoic acid.

3. The method of claim 1 wherein the nutrient-rich cells are selected from the group consisting of algae, yeast, and bacteria.

4. The method of claim 3 wherein the nutrient-rich cells are Haematococcus pluvialis.

5. The method of claim 4 wherein the nutrient is astaxanthin.

6. The method of claim 1 further comprising cooling the nutrient-rich cells during the milling.

7. The method of claim 6 wherein the cooling the nutrient-rich cells during the milling includes cooling the attrition mill.

8. The method of claim 1, wherein the nutrient is astaxanthin and the average grain size of the astaxanthin is reduced to approximately the size of a single astaxanthin molecule.

9. The method of claim 1 further comprising separating the ethanol from the nutrient.

10. The method of claim 1 further comprising prior to milling the nutrient-rich cell biomass in the ethanol and under the inert gas, supplying an additional ingredient to the interior of the attrition mill, the additional ingredient being selected from the group consisting of astaxanthin, eicosapentaenoic acid, and docosahexaenoic acid.

11. The method of claim 3 wherein the nutrient-rich cells are selected from the group consisting of *Phaedactylum tricornutum, Spirulina, Chlorella, Nannochloropsis, Monodus subterraneus, Crypthecodinium cohnii, Schizochytrium, Thraustochytrium aggregatum*, and *Ulkenia* sp.

12. The method of claim 3 wherein the nutrient-rich cells are *Phaffia rhodozyma*.

13. The method of claim 1 wherein the average grain size of the nutrient is reduced to less than 35 nm.

14. The method of claim 1 wherein the milling is conducted at a paddle speed of approximately 50 to 800 revolutions per minute.

15. The method of claim 1 wherein the media is selected from the group consisting of zirconia, alumina, and combinations thereof.

16. The method of claim 1 wherein the ethanol and the inert gas limit the oxidation of the nutrient to substantially no oxidation.

* * * * *